United States Patent [19]

Merrick

[11] Patent Number: 4,854,326

[45] Date of Patent: Aug. 8, 1989

[54] ESTABLISHING A ZERO REFERENCE FOR INVASIVE PRESSURE SENSORS

[75] Inventor: Edwin B. Merrick, Stow, Mass.

[73] Assignee: Hewlett-Packard Company, Palo Alto, Calif.

[21] Appl. No.: 290,818

[22] Filed: Dec. 22, 1988

Related U.S. Application Data

[63] Continuation of Ser. No. 38,427, Apr. 14, 1987, abandoned, which is a continuation of Ser. No. 802,296, Nov. 27, 1985, abandoned.

[51] Int. Cl.$^4$ .............................................. A61B 5/02
[52] U.S. Cl. .................................................... 128/675
[58] Field of Search ............... 128/645, 650, 670, 672, 128/692, 714, 748

[56] References Cited

U.S. PATENT DOCUMENTS

| 3,865,100 | 2/1975 | Ranai et al. | 128/675 |
|---|---|---|---|
| 3,939,823 | 2/1976 | Kaye et al. | 128/748 |
| 3,996,926 | 12/1976 | Birnbaum | 128/673 |
| 4,227,420 | 10/1980 | Lamadrid | 128/675 |
| 4,297,890 | 11/1981 | Hok | 128/673 |
| 4,413,528 | 11/1983 | Hok et al. | 128/675 |
| 4,431,009 | 2/1984 | Marino et al. | 128/675 |
| 4,456,013 | 6/1984 | De Rossi et al. | 128/675 |
| 4,459,841 | 7/1984 | Hok | 73/4 S |
| 4,475,556 | 10/1984 | Reiff | 128/673 |
| 4,545,389 | 10/1985 | Schabery et al. | 128/675 |
| 4,572,204 | 2/1986 | Stephens | 128/675 |
| 4,672,974 | 6/1987 | Lee | 128/673 |

FOREIGN PATENT DOCUMENTS

82/02657 8/1982 PCT Int'l Appl. ................. 128/672
1206255 9/1970 United Kingdom .

Primary Examiner—Max Hindenburg
Attorney, Agent, or Firm—Donald N. Timbie

[57] ABSTRACT

A catheter for use in apparatus for deriving a signal corresponding to the blood pressure of a patient, said catheter comprising means defining a lumen in said catheter, a transducer mounted at a distal end of said lumen, and a compliance means in said lumen.

4 Claims, 2 Drawing Sheets

ESTABLISHING A ZERO REFERENCE FOR INVASIVE PRESSURE SENSORS

CROSS REFERENCE TO RELATED APPLICATION

This application is a continuation of application Ser. No. 038,427, filed 4/14/87, now abandoned.

BACKGROUND OF THE INVENTION

The most accurate way of measuring the blood pressure in the heart or other internal organ of a patient is to insert a catheter having a transducer at its distal end through a blood vessel to the point of interest, but this increases the risk of blood clots and may abrade tissue near the heart. Current practice avoids these problems by coupling blood pressure at a peripheral site, such as in the wrist, to a transducer outside of the patient's body with a saline-filled lumen in a catheter. In the illustration of this technique shown in FIG. 1, an external transducer T is shown having a hollow pressure dome D that is mounted so as to apply the pressure in the dome D to a sensing surface 2 that translates the pressure into a corresponding signal on output leads $L_1$ and $L_2$. Excitation is applied to the transducer T via leads $L_3$ and $L_4$. A tube 4 that communicates with the interior of the dome D is connected via a valve $V_1$ to a tube 6. Another tube 8 that communicates with the dome D is connected via a valve $V_2$ to a lumen L in a catheter C, and the distal end of the catheter C is inserted into a blood vessel in the arm A of a patient P.

In use, the tubes 4, 6 and 8, the valves $V_1$ and $V_2$, the catheter C and the dome D are filled with a saline solution having nearly the same density as blood, and the catheter C is inserted into a blood vessel in the arm A of a patient P, e.g., in his wrist. The open end of the tube 6 is placed on a reference level indicated by the dashed line R that passes through the point at which the pressure is desired in the organ O. The valve $V_2$ is closed and the valve $V_1$ is opened. The signal on the leads $L_1$ and $L_2$ under this condition includes a first component due to the height of solution in the tube 6, in the tube 4 and in the valve $V_1$ above the sensing surface 2 and a second component called "transducer offset" that may add to or subtract from the first that is different for each transducer. The monitor or other device to which the leads $L_1$ and $L_2$ are coupled is then adjusted to a reading of zero pressure. Note that an opening B in the body of the transducer T permits atmospheric pressure to reach the underside of the sensing surface 2 so as to balance the effect of atmospheric pressure at the open end of the tube 6. Instead of manually adjusting the monitor to zero, the signal on $L_1$ and $L_2$ may be stored in a memory for numerical subtraction. Then the valve $V_1$ is closed and the valve $V_2$ opened so that the blood pressure of the patient at the organ O may be measured. A change in the height of the point in the arm A where the distal end of the catheter C is located has no effect on the pressure indicated by the transducer T.

A severe difficulty with such apparatus is that the compliance of the walls of the catheter C and the transducer T, as well as the inertia of the saline solution, impairs the frequency response so that the fidelity of the signal on the leads $L_1$ and $L_2$ is significantly less than optimum.

In order to improve accuracy, it has been proposed that the transducer be placed in a blood vessel in the body at a site remote from the organ generating the pressure of interest. However, a new problem arises. Consider the case of a catheter inserted into the radial artery in the wrist of a human patient for the purpose of indicating the pressure in the aorta. In this situation, the transducer is advanced only a few inches beyond the patient's wrist toward the heart. If the patient elevates his arm such that the transducer is raised by 13.8 mm, the associated instrumentation will indicate a pressure decrease of 1 mm Hg. If one assumes that a patient has the ability to vary his wrist elevation by ±1.0 meter, then a pressure measurement error of ±72 mm Hg can result. One obvious solution to this problem is to strap the patient's wrist to his body at the level of the organ so as to prevent the patient from moving his arm. Even this extreme measure has its limitations since patients may roll or be rolled from side to side to prevent fluid pooling in the lungs and for other reasons. This orientation change would also change the elevation relationship between the organ and the transducer site and introduce an error.

BRIEF DESCRIPTION OF THE INVENTION

Apparatus for measuring blood pressure in accordance with this invention is comprised of a reservoir for liquid, a catheter having at least one lumen therein, one end of the lumen being coupled to the reservoir; a transducer mounted at the distal end of the catheter in pressure communication with the distal end of the lumen; and preferably, compliance means such as a bubble of gas contained within the lumen so as to prevent deflection of the transducer diaphragm from exciting a fluid resonance between it, the fluid in the lumen, and the compliance of the lumen walls.

In use, the distal end of the catheter in which the transducer is mounted is inserted into a blood vessel in a limb of the patient, e.g., in his wrist. If the level of liquid in the reservoir is kept at the same level as the part in the body at which the blood pressure is being observed, the hydrostatic pressure applied via the lumen and compliance means to one side of the transducer is the same as the hydrostatic pressure applied to the other side by the blood, regardless of the position of the wrist, so that the only unbalanced variations in pressure applied to the transducer are those occurring at the point of interest. The purpose of the compliance means or fluid impedance means in the liquid path in the lumen is to prevent deflection of the transducer diaphragm from exciting resonance between the diaphragm, the liquid in the lumen and the compliance of the walls of the lumen.

DETAILED DESCRIPTION OF THE INVENTION

Figure 1:
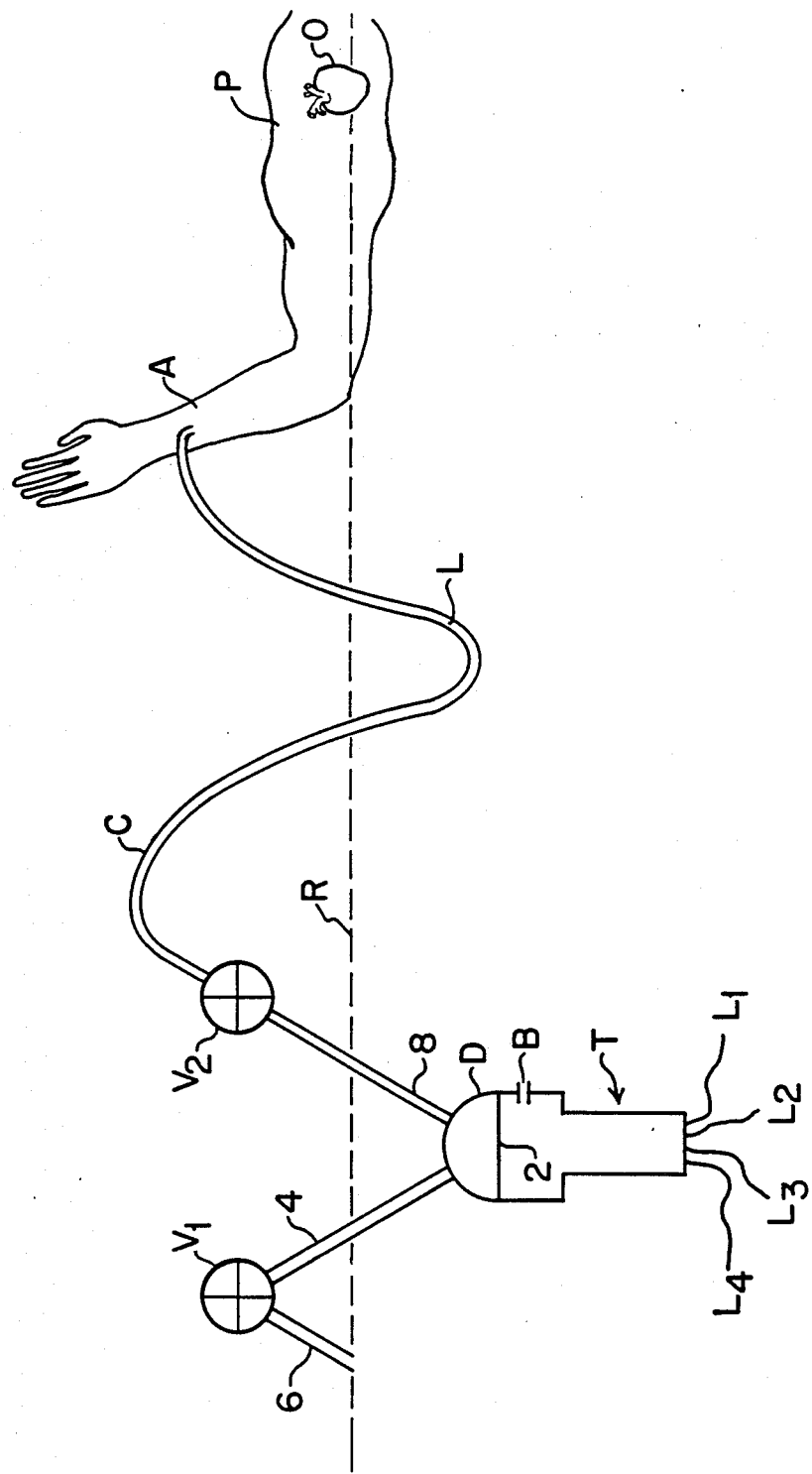
FIG. 1 illustrates a prior art system for measuring blood pressure.
Figure 2:
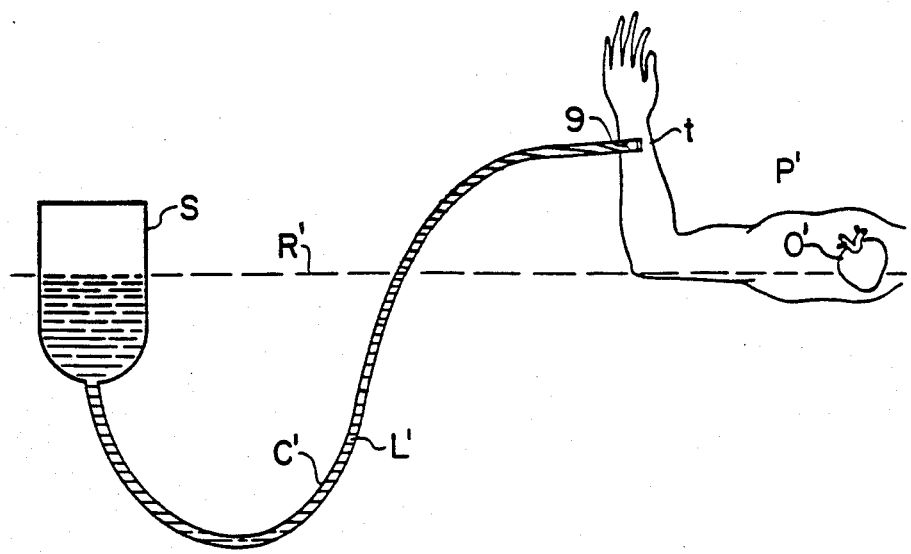
FIG. 2 illustrates a system incorporating the invention.

In FIG. 2, components corresponding to FIG. 1 are identified by the same letter primed. A reservoir S containing liquid that preferably has the same density as blood is shown as being connected to a transducer t via a catheter C' having a lumen L' therein. The lumen L' is filled with the same liquid as the reservoir S, and the level of the liquid in the reservoir S is preferably placed at the reference level R' which is at the same level as the point in the organ O' of the body of a patient P at which the pressure is to be indicated. In this particular embodiment, a compliance means in the form of gas retained by a floppy membrane 9 is located in the liquid-filled path in the lumen L' between the reservoir S and the transducer t, and the space between the membrane 9 and the trasnducer t is filled with gas at ambient pressure. This prevents oscillating movement of the liquid in the lumen L' as a result of interchange of energy via the liquid between the displacement of a diaphragm, not shown, in the transducer t and the compliance of the walls of the lumen L'. Any suitable means can be used to energize the transducer t and derive information bearing signals from it.

Figure 2A:
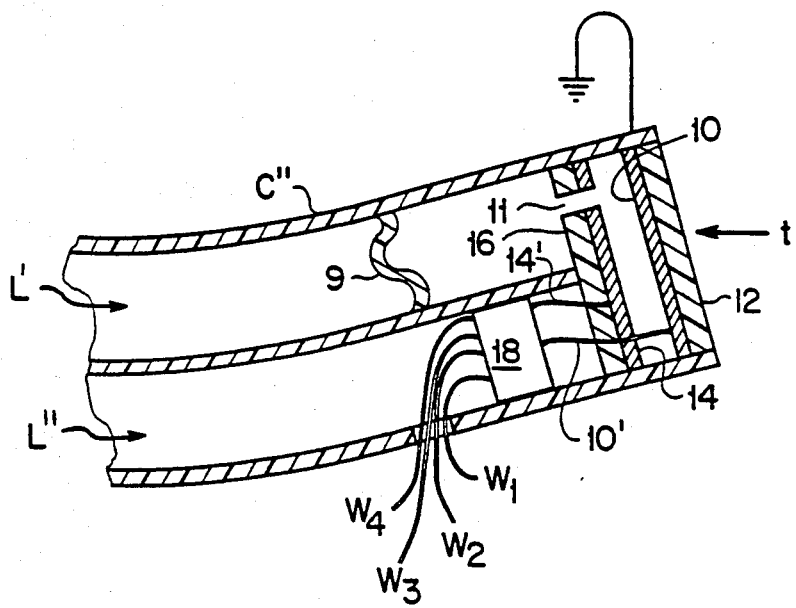
FIG. 2A is an enlarged view of the distal end of the catheter when one type of compliance means that might be used.

FIG. 2A is a detailed cross-sectional view of the distal end of the catheter C', the floppy membrane 9 and transducer t of an embodiment of the invention that is similar to that of FIG. 2 except that its catheter C" contains an additional lumen L' through which wires carrying power to the transducer t and signals derived from it may be passed. The transducer t may take many forms but in FIG. 2A it is shown as being comprised of a metal coating 10 on the inner surface of a flexible non-conductive plastic diaphragm 12 having an outer surface that is to be exposed to the blood pressure. A metal coating 14 is formed on a surface of an inflexible non-conducting bulkhead 16 and is separated from the metal coating 10 by a small space. A passageway 11 is provided through the bulkhead 16 and its metal coating 14. The space between the floppy membrane 9 and the metal coatings 10 and 14 is filled with gas at ambient pressure. The two metal coatings 10 and 14 form a capacitor whose capacitance is varied in accordance with the flexing of the diaphragm 12 by the blood pressure. An insulated lead 10' that passes through the metal coating 14 and bulkhead 16 connects the metal coating 10 to a circuit contained in a block 18 within the lumen L', and an insulated lead 14' that passes through the bulkhead 16 connects the coating 14 to the circuit in the block 18. The circuit functions to convert variations in the capacitance between the coatings 10 and 14 into an electrical signal which is placed on leads $W_1$ and $W_2$. Energization of the circuit is via leads $W_3$ and $W_4$. Whereas many circuits are known for performing this function, the one shown in my U.S. Pat. No. 4,546,651 issued on Oct. 15, 1985, and entitled "Transducer Coupling" would serve very well. The inside of the diaphragm 12 having the metal coating 10 is called the "reference side" of the diaphragm 12, and the other side is called the "active side". The active side is to be exposed to the blood pressure.

The gas pressure applied via the passageway 11 to the reference side of the diaphragm 12 is the same as any hydraulic pressure exerted by the liquid in the lumen L' on the floppy membrane 9 and is also the same as the hydraulic pressure applied via the blood to the active side of the diaphragm 12. If a patient's arm is moved so as to raise the transducer t above the reference level R', both hydraulic pressure are reduced by the same amount; and if the arm moves so as to lower the transducer t below the reference level R', both hydraulic pressures increase by the same amount. In either case, the hydraulic pressures cancel one another so that the only unbalanced pressure applied to the diaphragm 12 is the blood pressure at the organ O'.

In this particular embodiment of the invention, the compliance means is comprised of gas retained by the floppy membrane 9 sealed across the lumen L a short distance from the bulkhead 16. The space between it and the metal coatings 10 and 14 is filled with gas. Among the alternatives for the structure of the compliance means would be the inclusion of a soft closed cell foam elastomer in the lumen L', soft compliant walls in the lumen L' itself, or a drop or two of oil such as silicone oil in the liquid in the lumen L so as to retain a gas bubble. With any suitable compliance means in the lumen L', there is little resonance between the compliance of the diaphragm 12, the mass of the liquid in the lumen L' and the compliance of the walls of the lumen L'.

What is claimed is:

1. An apparatus for deriving a signal corresponding to liquid pressure in a patient comprising:
    means defining a passageway,
    a pressure to electric signal transducer mounted in one end of said passageway, said transducer having a diaphragm with an active side to which fluid pressure from a patient can be coupled and a reference side, said reference side being such that pressure applied to it via said passageway opposes pressure applied to said active side, said passageway having liquid between the reference side of said diaphragm and the end of said passageway that is remote from said transducer; and
    compliance means located within the means defining said passageway so as to damp oscillations that might result from interaction between the liquid, the means defining said passageway and said diaphragm in response to motion of said diaphragm thereby reducing the effect of such oscillation on the movement of said diaphragm.

2. In apparatus as set forth in claim 1 wheren said compliance means is formed by gas in said passageway adjacent the reference side of said diaphragm and oil between said gas and said liquid.

3. Apparatus for deriving a signal corresponding to the blood pressure of a patient comprising
    a catheter,
    means defining a lumen in said catheter,
    a transducer mounted in one end of said lumen, said transducer having a diaphragm, said diaphragm having an active side and a reference side,
    a reservoir for containing liquid, said reservoir being coupled to the other end of said lumen, and
    liquid contained in said lumen up to a point near said reference side of said diaphragm, and gas between said liquid and said diaphragm.

4. A catheter containing a lumen,
    an indwelling pressure transducer mounted in one end of said lumen, said transducer having a diaphragm, said diaphragm having an active side and a reference side, said reference side being in pressure communicating relationship with said lumen, and said lumen having liquid and a compliance means therein.

* * * * *